(12) United States Patent
Al-Ali et al.

(10) Patent No.: US 7,225,006 B2
(45) Date of Patent: May 29, 2007

(54) ATTACHMENT AND OPTICAL PROBE

(75) Inventors: Ammar Al-Ali, Tustin, CA (US);
Angela Grünhagen, Ilsfeld (DE)

(73) Assignee: Masimo Corporation, Irvine, CA (US)

( * ) Notice: Subject to any disclaimer, the term of this patent is extended or adjusted under 35 U.S.C. 154(b) by 390 days.

(21) Appl. No.: 10/350,550

(22) Filed: Jan. 23, 2003

(65) Prior Publication Data
US 2004/0147821 A1    Jul. 29, 2004

(51) Int. Cl.
*A61B 5/00*    (2006.01)

(52) U.S. Cl. .................................................. 600/344

(58) Field of Classification Search ............... 600/344, 600/310, 322, 323, 340, 473, 476
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,090,410 A * | 2/1992 | Saper et al. | 600/310 |
| 5,163,438 A | 11/1992 | Gordon et al. | |
| 5,337,744 A | 8/1994 | Branigan | |
| 5,425,357 A * | 6/1995 | Moll et al. | 600/207 |
| 5,431,170 A | 7/1995 | Mathews | |
| 5,437,275 A * | 8/1995 | Amundsen et al. | 600/323 |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,619,992 A * | 4/1997 | Guthrie et al. | 600/310 |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,673,693 A * | 10/1997 | Solenberger | 600/323 |

(Continued)

OTHER PUBLICATIONS

Masimo, "Anatomy of Quality Sensors," http://www.masimo.com/sensors/const.htm, 1 page downloaded and printed from the World Wide Web on or about Sep. 5, 2002.

(Continued)

*Primary Examiner*—Eric F. Winakur
(74) *Attorney, Agent, or Firm*—Knobbe, Martens, Olson & Bear, LLP

(57) ABSTRACT

A medical monitoring system, such as an oximetry system, applies an attachment for securing an optical probe to a measurement site. The attachment has an elongated support with a first end and a second end, and a dedicated area in proximity of the first end. The dedicated area receives an optical probe and includes a material that is transparent for light emitted and received by the optical probe. The dedicated area mountably receives the optical probe on the material so that in use, the material is positioned between the optical probe and a surface of a measurement site. The optical probe may be factory-mounted to the dedicated area of the attachment as a ready-to-use sensor. In the alternative, the attachment may be available as an individual component, or as a part of a kit including the attachment and the optical probe.

23 Claims, 4 Drawing Sheets

U.S. PATENT DOCUMENTS

| | | | |
|---|---|---|---|
| 5,685,299 | A | 11/1997 | Diab et al. |
| D393,830 | S | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,797,841 | A * | 8/1998 | Delonzor et al. ............ 600/323 |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,014,576 | A * | 1/2000 | Raley .......................... 600/344 |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,073,038 | A * | 6/2000 | Wang et al. ................ 600/323 |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,144,868 | A * | 11/2000 | Parker ......................... 600/344 |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,236,872 | B1 | 5/2001 | Diab et al. |
| 6,253,098 | B1 * | 6/2001 | Walker et al. ............... 600/344 |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,334,065 | B1 | 12/2001 | Al-Ali et al. |
| 6,349,228 | B1 | 2/2002 | Kiani et al. |
| 6,360,114 | B1 | 3/2002 | Diab et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,515,273 | B2 | 2/2003 | Al-Ali |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,597,933 | B2 | 7/2003 | Kiani et al. |
| 6,606,511 | B1 | 8/2003 | Ali et al. |
| 6,622,034 | B1 * | 9/2003 | Gorski et al. ................ 600/344 |
| 6,632,181 | B2 | 10/2003 | Flaherty et al. |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kianl et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,725,075 | B2 | 4/2004 | Al-Ali |
| 6,745,060 | B2 | 6/2004 | Diab et al. |
| 6,760,607 | B2 | 7/2004 | Al-All |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-All |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |

OTHER PUBLICATIONS

Masimo, "LNOP Single Patient Adhesive Latex-Free Sensors," http://www.masimo.com/sensors/adhesive.htm, 1 page downloaded and printed from the World Wide Web on or about Sep. 11, 2002.

Masimo, "Signal Extraction Technology," Technical Bulletin 1.

* cited by examiner

ATTACHMENT AND OPTICAL PROBE

BACKGROUND OF THE INVENTION

1. Field of the Invention

Embodiments of the present invention relate in general to optical probes that are secured to a measurement site during use. More particularly, the embodiments relate to optical probes that are secured to the measurement site by wrapping.

2. Description of the Related Art

An optical probe generally operates by measuring a light signal passed through a medium. In oximetry, the optical probe attaches to an oximeter system such that the oximeter system determines at least one characteristic of the medium. In the medical field, a pulse oximetry probe measures a light signal passed through tissue. For example, after passing through tissue, the light signal varies depending on the oxygen saturation of the blood in that tissue. The oximeter system processes the measured light signals from the pulse oximetry probe and can determine characteristics of the tissue, including, for example, a pulse rate, blood oxygen saturation, or the like. The pulse oximetry probe is typically placed on an extremity, such as a finger, toe, hand, or foot of the person being monitored.

Today, pulse oximetry is a widely accepted and successful non-invasive technique for monitoring characteristics of patients. In addition, the conventional pulse oximeter probe is manufactured in a wide number of shapes and sizes for neonatal, infant and adult applications. Generally, each shape and size typically employs adhesion-based, spring-tension-based, or hook-and-loop-based securing mechanisms to position and secure the optical probe to a measurement site.

However, the foregoing conventional securing mechanisms are often less than optimal in certain environments. For example, adhesive-based securing mechanisms can present adherence issues on surfaces that are wet and/or fluid-covered, such as infant skin immediately following birth. For example, in the baby born at or near term, skin coatings such as vernix can present adhesion problems, and in the preterm infant, adhesive-based sensors can irritate the infant's fragile skin.

Moreover, hook-and-loop-based securing mechanisms, such as Velcro® straps, can be applied incorrectly. Velcro®-based securing mechanisms often employ a multistep and multielement positioning and securing process in order to apply the optical probe to a measurement site. For example, the optical probe is often first placed on the measurement site. Thereafter, the Velcro® strap can be secured. In highly agitated environments, such as those associated with newborns, patient transport, exercise testing and ICU care, a multistep process is burdensome and often difficult for the clinician.

In addition to the forgoing infant concerns, environments including severely damaged and/or sensitive tissue, such as burns or the like, can pose a number of problems for the conventional securing mechanisms. For example, adhesive-based securing mechanisms may affix themselves to fragile newly healed skin such that removal of the adhesive may cause the skin to tear, thereby redamaging the tissue and causing pain to the patient. Spring-tension-based or pressure-based securing mechanisms, such as a clothespin-type clip mechanism, may not allow the skin to optimally breathe, may restrict blood flow and are often recommended for short-term application.

Although conventional securing mechanisms are often unworkable in the foregoing environments, the need for non-invasive monitoring in those environments remains.

SUMMARY OF CERTAIN INVENTIVE EMBODIMENTS

Based on the foregoing, a need exists for a securing mechanism capable of functioning in environments where adhesive-based, spring-tension-based, and/or hook-and-loop-based securing mechanisms are often less effective.

Accordingly, one aspect of an embodiment involves an attachment for securing an optical probe to a measurement site. The attachment has an elongated support with a first end and a second end, and a dedicated area in proximity of the first end. The dedicated area receives an optical probe and includes a material that is transparent for light emitted and received by the optical probe. The dedicated area mountably receives the optical probe on the material so that in use, the material is positioned between the optical probe and a surface of a measurement site.

The optical probe may be factory-mounted to the dedicated area of the attachment as a ready-to-use sensor or probe. In the alternative, the attachment may be available as an individual component, or as a part of a kit including the attachment and the optical probe.

Another inventive aspect of another embodiment involves a pulse oximetry probe having an optical probe configured to emit and receive light, an elongated support having a first end and a second end, and at least one transparent window in proximity of the first end of the support and configured to receive the optical probe. The at least one transparent window receives the optical probe in a manner where application of the support to a measurement site positions at least a portion of the at least one transparent window on a measurement site-facing side of the optical probe.

A further inventive aspect involves a method of manufacturing an attachment for securing an optical probe to tissue at a measurement site in order to determine at least one characteristic of the tissue. An elongated support having a first end and a second end is provided and an area in proximity of the first end of the support is dedicated to receive an optical probe. A material is coupled to the area. The dedicated area is configured to mountably receive the optical probe on the material so that in use, the material is positioned below the optical probe and above a surface of a measurement site.

Another inventive aspect involves a method of manufacturing a pulse oximetry probe to be secured to tissue at a measurement site in order to determine at least one characteristic of the tissue. An elongated support having a first end and a second end is provided, and at least one transparent window is provided in proximity of the first end of the support. The optical probe is coupled to the at least one transparent window in a manner where application of the support to a measurement site positions at least a portion of the at least one transparent window on a measurement site-facing side of the optical probe.

An additional inventive aspect involves a method of securing an optical probe to tissue at a measurement site in order to determine at least one characteristic of the tissue. Elements of an optical probe are mounted on a transparent area of an attachment. The elements of the optical probe mounted on the attachment are positioned at a predetermined measurement site. The elements of the optical probe are secured to the predetermined measurement site by wrapping the attachment around the measurement site.

Another inventive aspect involves an oximetry system having an oximeter, an oximeter cable connectable to the oximeter, and a sensor connectable to the oximeter cable for communications with the oximeter. The sensor includes an optical prove configured to emit and receive light and to communicate with the oximeter, and an elongated support including a dedicated area and configured to receive the optical probe. The dedicated area includes a material that is transparent for light emitted and received by the optical probe, and is configured to mountably receive the optical probe on the material so that in use. The material is positioned between the optical probe and a surface of a measurement site.

BRIEF DESCRIPTION OF THE DRAWINGS

The present invention is described in more detail below in connection with the attached drawings, which are meant to illustrate and not limit the invention, and in which:

FIG. 2 illustrates a side view of the embodiment illustrated in FIG. 1a;

DETAILED DESCRIPTION OF CERTAIN INVENTIVE EMBODIMENTS

According to an embodiment, an attachment secures an optical probe to a measurement site in a wide variety of environments, including wet or fluid-covered measurement sites, damaged or sensitive measurement sites, or the like. In various embodiments, the attachment includes a transparent surface having a first side facing the measurement site and a second side opposite the measurement site. An optical probe can be removably affixed to the second side of the transparent surface in any suitable manner, including using adhesives present on many conventional optical probes.

After the optical probe is affixed to the attachment, the attachment secures the optical probe to the measurement site in a manner which avoids adhesive contact with fluid-covered or damaged skin. For example, the attachment may wrap the measurement site and attach to itself through adhesive, hook-and-loop mechanisms, snaps, buttons, elastic, or the like. Moreover, in one embodiment, the attachment is supplied with the optical probe. In another embodiment, the attachment is supplied independently.

To facilitate a complete understanding of various embodiments of the invention, the remainder of the detailed description describes exemplary embodiments with reference to the drawings, wherein like elements are referenced with like numerals throughout.

Figure 1A:
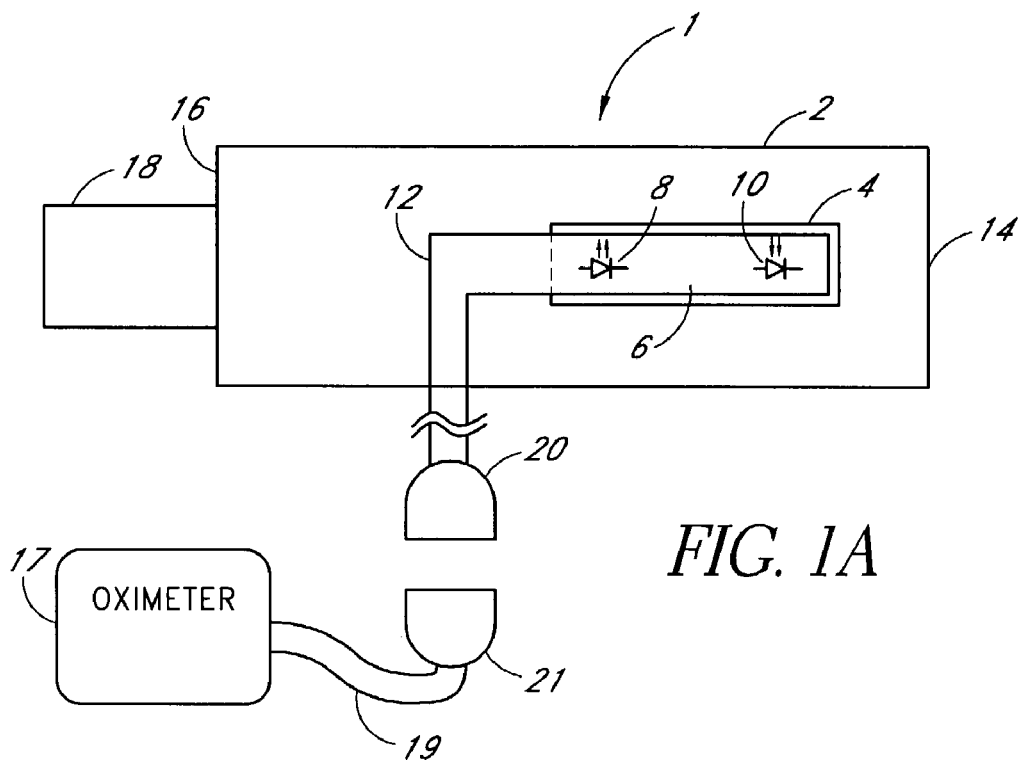
FIG. 1a is an illustration of an embodiment of an attachment with a mounted optical probe.

FIG. 1a is an illustration of one embodiment of an attachment 1 for an optical probe 6. The attachment 1 is configured to secure the optical probe 6 to a measurement site of a patient, such as a foot, toe, hand, finger or arm. The optical probe 6 preferably measures at least one light signal passed through tissue at the measurement site. The optical probe 6 communicates with a monitoring device, such as an oximeter 17, to process the measured light signal to determine at least one characteristic of the tissue. For example, in an oximetry system, the oximeter 17 may determine one or more of the patient's pulse rate, blood oxygen saturation, or the like, at the measurement site.

As described below in greater detail, the optical probe 6 is mountable to the attachment 1 using, for example, an adhesive. In one embodiment, as the attachment 1 secures the mounted optical probe 6 to the measurement site, no adhesive contacts fluid-covered or damaged portions of the measurement site. Thus, the attachment 1 becomes a fastening mechanism for the optical probe 6, rather than the optical probe 6 itself. The attachment 1 is advantageously suited for the problematic environments having fluids and/or sensitive skin issues. In addition, the attachment 1 provides for single element placement, in that the attachment 1 with the mounted optical probe 6 preferably wraps around the patient's foot, toe, hand, finger or arm and positions the optical probe 6, all in the motion of wrapping the attachment 1 around the measurement site.

Figure 2:
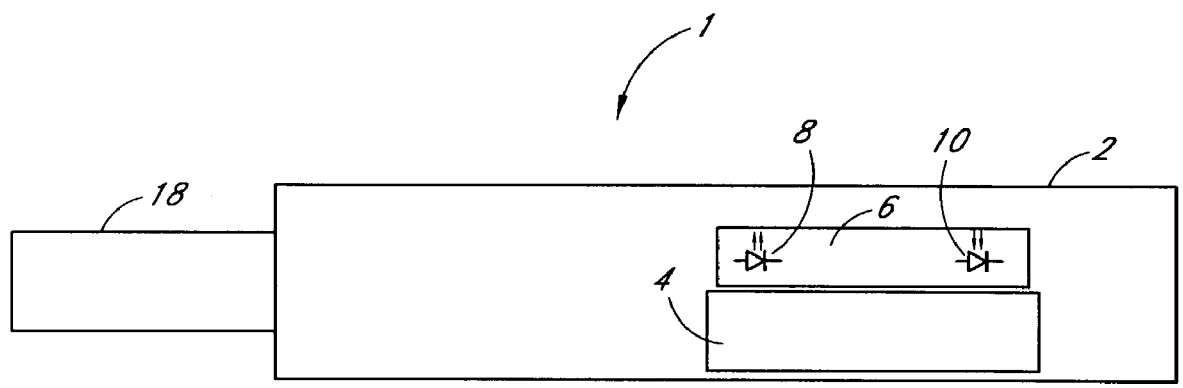

As shown in FIG. 1a and FIG. 2, which is a side view of the embodiment shown in FIG. 1a, the attachment 1 includes a support 2 having an elongate shape, a first end 14 and an opposite end 16 including a tongue 18. In one embodiment, the support 2 is a soft foam padding, such as, for example, foam padding commercially available, for example, from J.T. Posey Company. The tongue 18, for example, has hooks that interact with loops on one side of the padding to provide for a "hook and loop" closure when the support 2 is wrapped around a patient's extremity, such as a foot of an infant. In other embodiments, the tongue 18 and the support 2 may be configured to secure the attachment 1 through adhesive, adhesive tape, snaps, buttons, elastic, or the like.

In the illustrated embodiment, the tongue 18 is smaller and thinner than the support 2, and may be of a different material than the support 2. Further, the tongue 18 may be sewn, glued or welded to the support 2.

It is contemplated that the support 2 has a length selected for a particular application. For example, in neonatal or infant applications the length of the support is typically shorter than in adult applications. Depending on the application, the length may vary between about 4 inches for a neonatal application and about 10 inches for an adult application. Similarly, the width of the support 2 may vary between infant and adult applications. An exemplary width is about 1 inch. Further, the thickness of the support 2 is may vary depending on the selected material. However, a skilled artisan will recognize from the disclosure herein that the dimensions thereof may vary widely depending on, for example, particular applications and patients, costs of manufacture, or the like. Moreover, as to the particular dimensions of the optical probe 6, those skilled in the art will appreciate that the illustrated embodiments are not to scale and are also subject to particular applications and patients, or the like.

In proximity of the first end 14, the support 2 has a dedicated area 4 to receive the optical probe 6. The dedicated area 4 includes a material that is transparent for light emitted and received by the optical probe 6. Those skilled in the art will appreciate that the term "light," as used herein, generally relates to electromagnetic energy, whether visible or invisible. For example, pulse oximetry typically uses red light and infrared light to determine the characteristics of the tissue. Accordingly, in one embodiment, the transparent material is transparent for red light and infrared light. In another embodiment, the transparent material may have predetermined filter characteristics designed to reduce noise.

The material may be a flexible and transparent plastic material, such as, for example, PVC, acetate, polyethylene, or polyester. The material may have a thickness of between about 0.001 and 0.007 inches.

In one embodiment, the dedicated area 4 is manufactured by cutting or punching an opening of appropriate size into the soft foam padding. In a subsequent step, the transparent material is then glued, sewn, or both, into the area of the opening. For example, the transparent material may be sized to overlap with edges of the opening and sewn to the soft foam padding. Overlapping may also be advantageous if the materials are glued together.

Figure 1B:
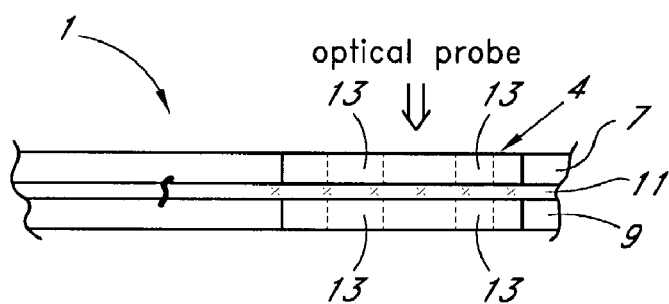
FIG. 1b is an illustration of an embodiment of an attachment having a bottom layer, a top layer and a layer of transparent material between the bottom and top layers.

In another embodiment, the attachment 1 includes several layers of material, as shown in FIG. 1b. For example, a layer 11 of transparent material may be sandwiched between a bottom layer 9 and a top layer 7. The bottom layer 9 and the top layer 7 each have at least one opening or window within the dedicated area 4. The transparent material is positioned between the bottom layer 9 and the top layer 7 and covers the at least one opening or window. As indicated in FIG. 1b, the optical probe 6 is positioned from a side that is opposite the measurement-site facing side of the attachment 1. The optical probe 6 may be positioned on the top layer 7 or on the layer 11 of transparent material.

It is contemplated that the attachment 1 may have one window, for example, as shown in FIG. 1a, or two windows 13, one for the emitter 8 and one for the detector 10, as indicated in FIG. 1b through dashed lines in the top and bottom layers 7, 9. The window or the windows may be cut out or punched out from the top and bottom layers 7, 9. Further, it is contemplated that the material of the top and bottom layers 7, 9 may be a soft foam padding. In another embodiment, the material of the bottom layer 9 may be a soft foam padding and the material of the top layer 7 may be a material other than soft foam padding, for example, a fabric material. The attachment 1 may be secured to the measurement site through a "hook and loop" closure, as described above. In other embodiments, the attachment 1 may be secured through adhesive, adhesive tape, snaps, buttons, elastic, or the like.

Figure 1C:
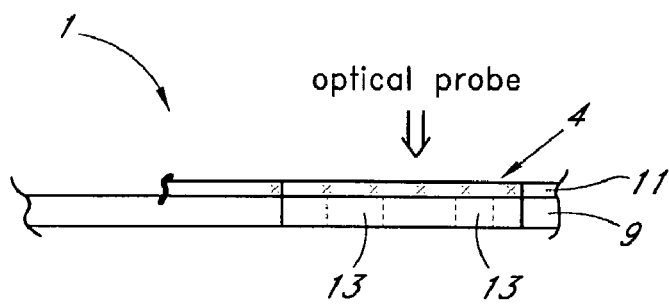
FIG. 1c is an illustration of an embodiment of an attachment having a bottom layer and a layer of transparent material.

In a further embodiment shown in FIG. 1c, the attachment 1 may include a bottom layer 9 and a layer 11 of the transparent material, which forms the top layer of the attachment 1. The bottom layer 9 may include one or more windows that the transparent material covers. The transparent material is positioned on a rear surface of the bottom layer 9 that is opposite the measurement site facing side. The transparent material may extend over all or only a part of the rear surface. The attachment 1 may be secured to the measurement site through a "hook and loop" closure, adhesive, adhesive tape, snaps, buttons, elastic, or the like The various layers of the attachment 1 may be sewn together. In other embodiments, the layers may be glued, or glued and sewn. Those skilled in the art will appreciate that any other suitable manner of combining the materials of the attachment 1 may be used, such as welding, heat compression, or the like.

As shown in the embodiment of FIG. 1a, the dedicated area 4 may be larger than an area covered by the optical probe 6. Those skilled in the art will appreciate that the dedicated area 4 and the area covered by the optical probe 6 may be similar, and that the dedicated area 4 may in certain embodiments be smaller than the area covered by the optical probe 6. Generally, the size of the dedicated area 4 is selected to allow unobstructed passage of light from and to the optical probe 6.

According to one embodiment, the optical probe 6 has several elements including an emitter 8 and a detector 10. The optical probe 6 preferably communicates with the oximeter 17 through, for example, connectors 20, 21, a cable 19 and a flex circuit 12. The emitter 8 and the detector 10 are mounted to the flex circuit 12. The flex circuit 12 preferably connects the connector 20 to the emitter 8 and the detector 10 such that the appropriate electrical drive and detection signals are communicated to and from the oximeter 17. In one embodiment, the flex circuit 12 includes a flexible base material and electrical conductors. The flexible base material may be a plastic material, such as polyimide, or the like. The electrical conductors may be defined, for example, in one or more layers of copper on the base material. However, a skilled artisan will recognize from the disclosure herein that the flex circuit 12 may straightforwardly comprise wires or other electrical conductors.

In the illustrated embodiment, the flex circuit 12 has a bent configuration, where a first part supports the emitter 8 and the detector 10, and a second part connects to the connector 20. The second part extends in a direction substantially perpendicular from the optical probe 6 and is substantially in the same plane as the detector 10. It is contemplated that in other embodiments the second part of the flex circuit 12 may extend in other directions.

According to one embodiment, the emitter 8 and the detector 10 are mounted to a tape material with adhesive on a bottom side. It is contemplated that the emitter 8 and the detector 10 are mounted so that no tape obstructs the passages of light through tissue. The tape material secures the emitter 8 and the detector 10, for example, to the transparent material of the dedicated area 4 and supports electrical wiring that connects the emitter 8 and the detector 10 to the flex circuit 12. It is contemplated that in another embodiment the emitter 8 and the detector 10 may not be mounted on a tape and may instead be mounted individually on the transparent material. Further, in an embodiment in which the support 2 has separate windows for the emitter 8 and the detector 10, the optical probe 6 may be mounted on the material of the support 2 without obstructing the passage of light.

The emitter 8 and the detector 10 are spaced apart so that, when applied to the measurement site, the emitter 8 is opposite to the detector 10 in order to detect light passed through the tissue. For example, for a neonatal foot application, the emitter 8 and the detector 10 are about 1 inch apart.

The attachment 1, the optical probe 6, or both, may have indicia to assist a healthcare provider to accurately apply the attachment 1 to the measurement site. For example, symbols may indicate the location of the emitter 8 and the detector 10. In certain applications, the attachment 1 secures the emitter 8 and the detector 10 so that the emitter 8 is opposite the detector 10.

A skilled artisan will recognize from the disclosure herein that there are a large number of shapes of the attachment 1, the optical probe 6, along with a wide number of measurement sites, that may be chosen based to some degree on the relationship between the optical probe 6 and the measurement site. For example, a probe that is based on light reflection instead of light transmission may advantageously be mounted along the skin surface so that the emitter and the detector are substantially at the same level.

The optical probe 6 may be based on a LNOP® adhesive sensor available from Masimo Corporation. Such LNOP® sensors are designed to reduce interference from physiologic and non-physiologic noise. For example, the detector is recessed in a cavity that protects the detector from ambient light interference. Further details as to the electrical and optical properties of the optical probe 6 are described in data sheets available from Masimo Corporation.

In use, the transparent material within the dedicated area 4 separates the optical probe 6 from the tissue at the measurement site. In one embodiment, the support 2 and the transparent material are in contact with the skin. The surfaces of the support 2 and the transparent material, which are in contact with the skin, can be selected to be non-stick, non-irritant and hypoallergenic to infant or adult skin.

Figure 3:
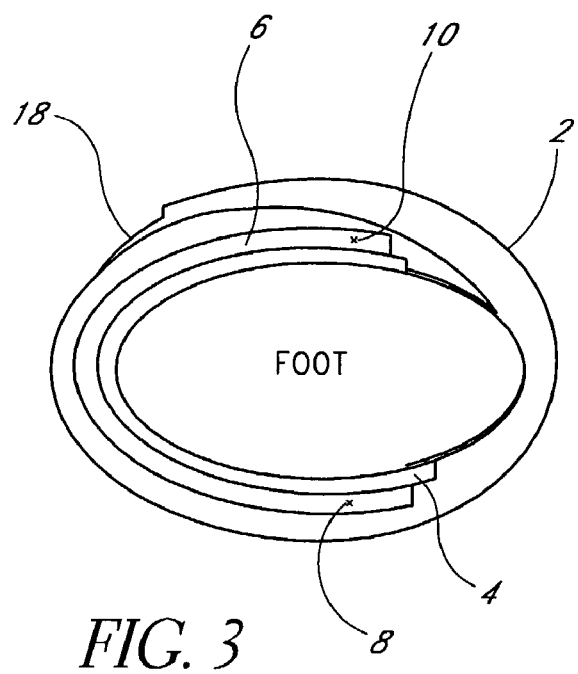
FIG. 3 illustrates the attachment of FIG. 1a applying an optical probe to a measurement site of a patient.

FIG. 3 illustrates an embodiment of an attachment 1 that secures an optical probe 6 to a measurement site of a patient. For example, a healthcare provider positions the optical probe 6 so that the emitter 8 and the detector 10 are substantially opposite to each other, wraps the support 2 around the measurement site, and secures the tongue 18 to a surface of the support 2. As illustrated, the transparent material is positioned between the patient's skin and the optical probe 6.

It is contemplated that in certain embodiments, the support 2 may comprise material that helps isolate the optical probe 6 from ambient light, thereby improving the signal-to-noise ratio. For example, the material may include black plastic films, such as, for example, those commercially available from E.I. du Pont de Nemours and Company. The material may include metal foils or thick foams, such as, for example, those commercially available from 3M, or the material may include metallized plastic films, such as, for example, those commercially available from Astral Technologies.

Although the foregoing has disclosed the attachment 1 in terms of preferred and alternative embodiments, a skilled artisan will recognize from the disclosure herein a wide number of advantageous materials, shapes, sizes, and manners of operation. For example, the tongue 18 may comprise an adhesive, a snap, buttons, or an elastic instead of a hook-and-loop mechanism. Moreover, the tongue 18 may comprise a stretch fabric material. The foregoing embodiments of the tongue 18 allow adjustment of the attachment 1 to varying sizes of the measurement site. Further, it is contemplated that the attachment 1 may be initially sterile or sterilized for use in medical environments where sterilization is preferred.

The foregoing attachment 1 is advantageously suited for monitoring newly delivered infants. As discussed in the foregoing, the use of the optical probe 6 in such an environment allows for continuous and increased accuracy in patient monitoring. For example, one embodiment may include one or more audio or visual alarms on the oximeter system.

Figure 4:
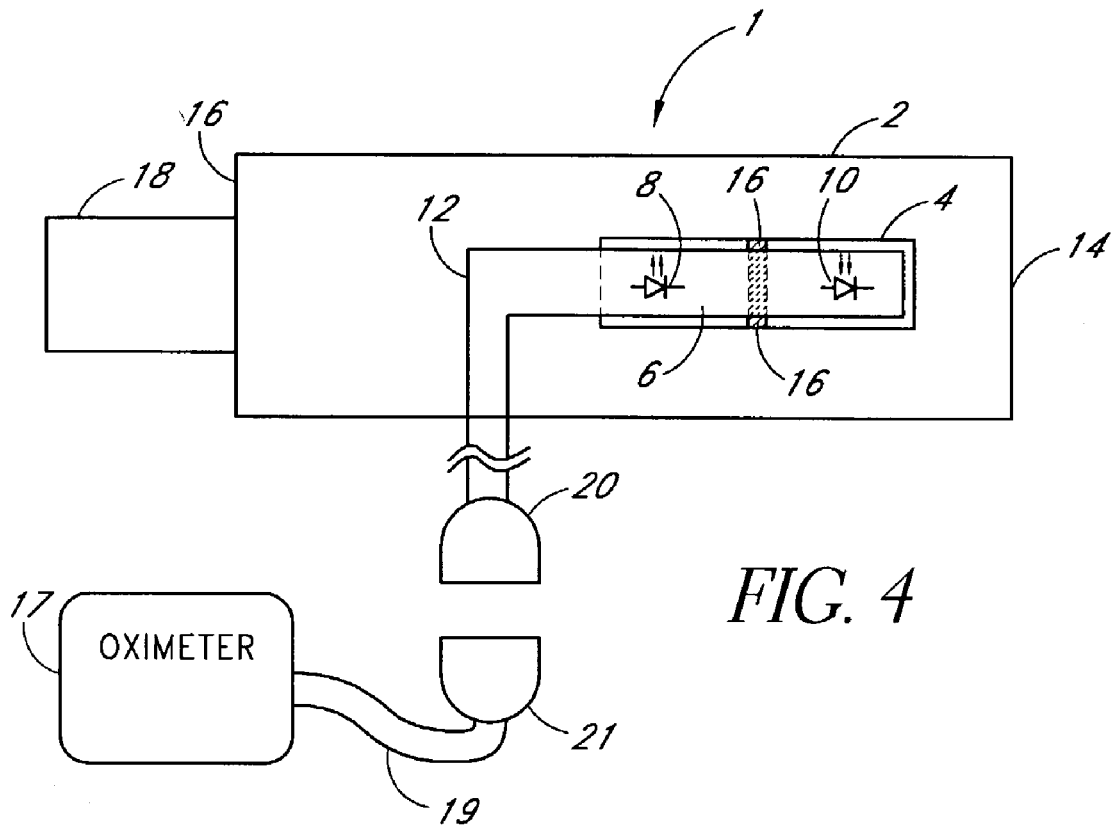
FIG. 4 is an illustration of an embodiment of an attachment configured to reduce light piping.

FIG. 4 is an illustration of another embodiment of an attachment 1 for an optical probe 6. The embodiment shown in FIG. 4 is generally based on the embodiments described above with respect to FIGS. 1, 2 and 3. The transparent material within the dedicated area 4, however, is modified in order to reduce noise received by the detector 10 by reducing light piping. In the illustrated embodiment, the transparent material includes an opaque material 16 that can be shaped, for example, as a stripe that extends between the longitudinal sides of the transparent material.

The opaque material 16 is selected to reduce or block light emitted from the emitter 8 from reaching the detector 10 without passing through tissue at the measurement site. Thus, the opaque material 16 interrupts a light path along the transparent material.

Figure 5:
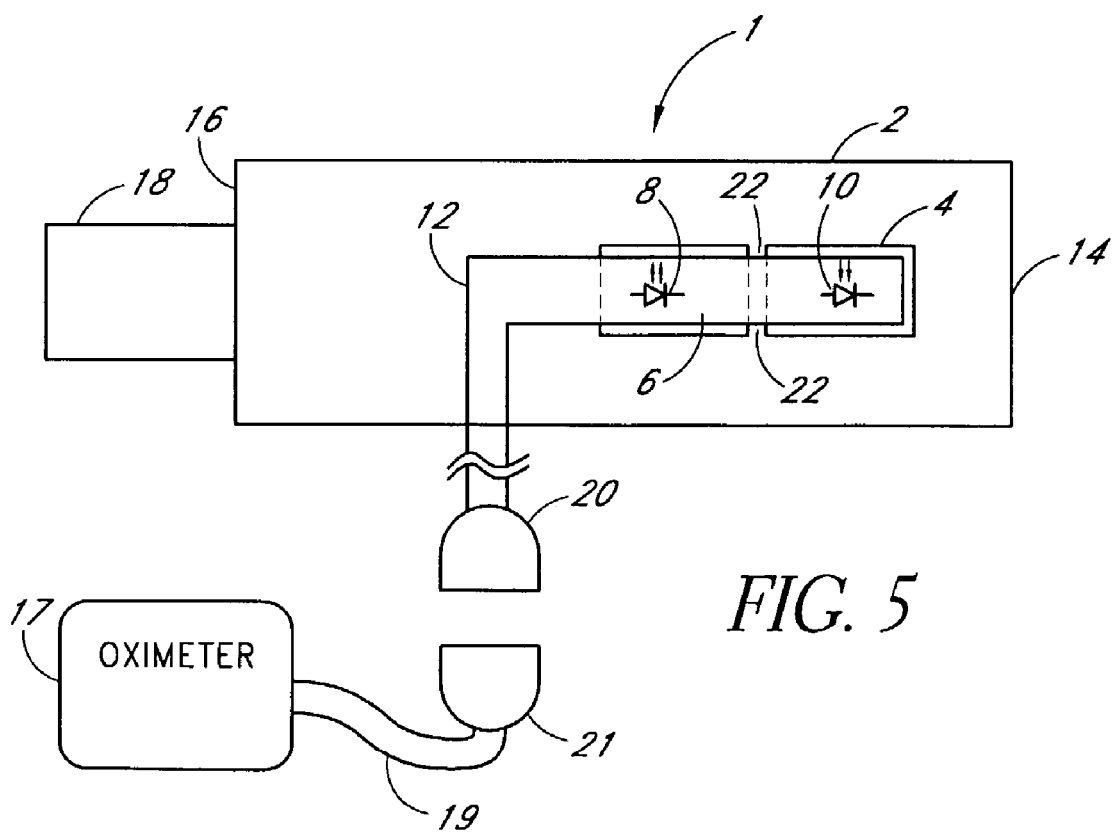
FIG. 5 is an illustration of another embodiment of an attachment configured to reduce light piping.

FIG. 5 is an illustration of another embodiment of an attachment 1 that reduces light piping. Similar to the embodiment shown in FIG. 4, the embodiment shown in FIG. 5 reduces an amount of light that can reach the detector 10 without first passing through the tissue. According to an embodiment, the transparent material includes a two-part element, wherein the two parts are located at a distance 22 to each other. In one embodiment, the distance 22 is a gap, for example, an air gap. In another embodiment, the material of the support 2 separates the two pieces. For example, two openings may be punched or cut out from the support 2 and the two parts of transparent material may be glued, sewn, or both, in the openings. In yet another embodiment, an opaque material may be provided between the two parts within the distance 22. The opaque material may be similar to the opaque material used in the embodiment of FIG. 4.

Figure 6:
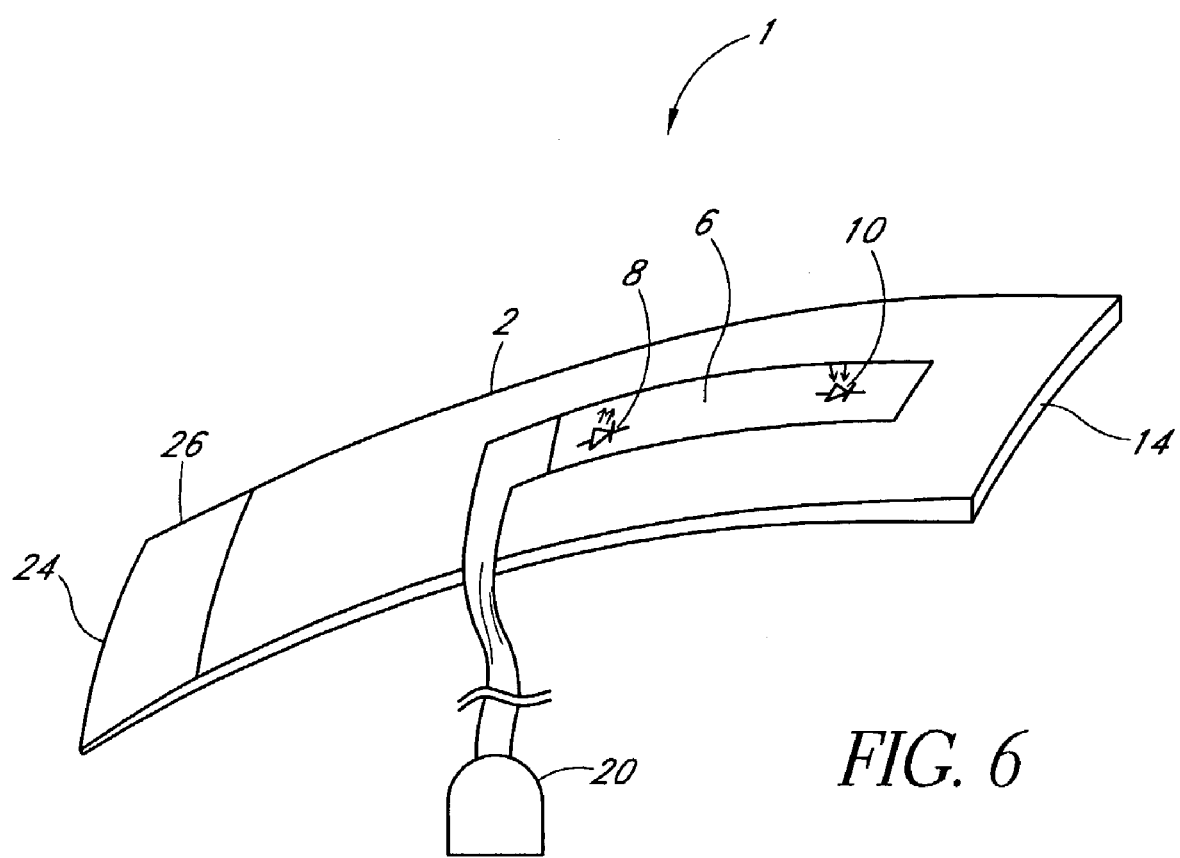
FIG. 6 is an illustration of an embodiment of an attachment configured as a tape.

FIG. 6 is an illustration of an attachment 1 wherein the support 2 is a tape. In proximity to the first end 14, the optical probe 6 is mounted to the support 2. For example, the optical probe 6 has an adhesive covered bottom surface that attaches to a top surface of the tape. At an end 24 opposite the end 14, the support 2 has an adhesive area 26 at a bottom surface of the tape that attaches to the top surface of the tape when applied to the measurement site. The bottom surface, other than the adhesive area 26, does not include an adhesive. The application of the attachment 1 shown in FIG. 6 to a measurement site is similar to the application of the attachment 1 shown in FIG. 3 and described with reference to FIG. 3.

In one embodiment, the support 2 is a transparent tape that may be cut to a desired length. Within the adhesive area 26, the support 2 is less transparent or opaque. In an alternative embodiment, the support 2 is an opaque tape that is transparent in a dedicated area where the optical probe 6 is mounted. Further, the opaque tape may have punched out openings in an area where the emitter 8 and the detector 10 of the optical probe 6 are mounted.

An advantage of the embodiments described with reference to FIGS. 1–6 is that the optical probe 6 may be factory-mounted to the dedicated area 4 of the attachment 1 as a ready-to-use sensor. In the alternative, the attachment 1 may be available as an individual component, or as a part of a kit including the attachment 1 and the optical probe 6. Before use, a healthcare provider mounts the optical probe 6 to the dedicated area 4 of the attachment 1. For example, a hospital may already have a large quantity of adhesive optical probes configured for the pulse oximeters used in the hospital. In that case, the hospital may continue using these adhesive optical probes by simply mounting them to individually-supplied attachments.

In addition to the preferred and alternate embodiments of the attachment 1, a skilled artisan will recognize that the attachment 1 may advantageously include any, some, or all of the features and aspects discussed in the foregoing description of FIGS. 1–6. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

What is claimed is:

1. A probe for non-adhesively attaching to a measurement site, comprising:

an elongated support having a first end and a second end, the support comprising:

at least one attachment element in proximity of one of said ends, wherein the at least one attachment element is configured to attach with a second portion of said support to non-adhesively secure an optical probe to a measurement site; and a dedicated area in proximity of the first end and configured to receive the optical probe, the dedicated area comprising a material different from said support that is transparent for light emitted and received by the optical probe; and a disposable optical probe comprising a standalone adhesive-type optical probe which is configured to adhesively attach to a measurement site independent of said support;

wherein the disposable optical probe is mounted on the dedicated area so that during measurement, the material is positioned between the optical probe and a surface of a measurement site.

2. The probe of claim 1, wherein the support is configured to allow wrapping the support around the measurement site.

3. The probe of claim 2, said attachment element comprising a tongue extending from the second end of the support.

4. The probe of claim 1, wherein the support includes a soft foam padding.

5. The probe of claim 4, said attachment element comprising a tongue extending from the second end of the support, the tongue comprising hooks to cooperate with a surface of the soft foam padding in a hook-loop securing mechanism.

6. The probe of claim 1, wherein the support includes a tape.

7. The probe of claim 6, said attachment element in proximity of the second end and comprising an adhesive to cooperate with a surface of the tape.

8. The probe of claim 1, wherein the dedicated area is sized to allow passage of light emitted and received by an optical probe.

9. The probe of claim 1, wherein the support has at least one opening, and wherein the material is coupled to the at least one opening.

10. The probe of claim 9, wherein the material is mounted within the at least one opening by at least one of sewing, gluing and welding.

11. The probe of claim 10, wherein the material is a two-part element, and wherein the parts are spaced apart at a predetermined distance.

12. The probe of claim 9, wherein the material includes an opaque portion that prevents light from traveling from one side of the material to another side of the material.

13. The probe of claim 12, wherein the material and the dedicated area have an elongate shape, and wherein the opaque portion comprises a stripe that extends between longitudinal sides of the material.

14. The probe of claim 1, wherein the material is a two-part element, and wherein the support has two openings, each opening sized to receive one of the parts.

15. The probe of claim 1, wherein the support comprises a bottom layer having a back surface and a bottom surface facing of the measurement site, and wherein at least a portion of the back surface supports the material.

16. The probe of claim 15, wherein the bottom layer has an opening, and wherein the material covers the opening.

17. The probe of claim 15, wherein the material is mounted to the back surface by at least one of sewing, gluing and welding.

18. The probe of claim 15, wherein the material includes an opaque material that reduces an amount of light that travels from one side of the material to another side of the material.

19. The probe of claim 18, wherein the material and the dedicated area have an elongate shape, and wherein the opaque portion comprises a stripe that extends between longitudinal sides of the material.

20. The probe of claim 15, wherein the bottom layer has two openings, each opening sized to allow passage of light, and wherein the material covers the openings.

21. The probe of claim 15, wherein the support further comprises a top layer, and wherein the transparent material is positioned between the top layer and the bottom layer.

22. The attachment of claim 1, wherein the disposable optical probe comprises a pulse oximetry disposable optical probe.

23. A method of securing an optical probe to tissue at a measurement site in order to determine at least one characteristic of the tissue, the method comprising:

mounting elements of a disposable optical probe on a transparent area of an attachment, wherein the optical probe comprises an adhesive-type optical probe capable of adhesive attachment to a measurement site independent of said attachment;

positioning elements of the optical probe mounted on the attachment at a measurement site; and wrapping the attachment around the measurement site and securing the elements of the optical probe to the measurement site by attaching a first portion of said attachment with a second portion thereof to non-adhesively secure the probe to the tissue.

* * * * *